United States Patent
Cross, Jr. et al.

[11] Patent Number: 5,935,159
[45] Date of Patent: *Aug. 10, 1999

[54] MEDICAL ELECTRICAL LEAD

[75] Inventors: Thomas E. Cross, Jr., St. Francis; Bret R. Shoberg, Corcoran; Alan C. Rausch, Brooklyn Park; Mark A. Hjelle, White Bear Lake, all of Minn.

[73] Assignee: Medtronic, Inc., Minneapolis, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/990,647

[22] Filed: Dec. 15, 1997

Related U.S. Application Data

[60] Provisional application No. 60/033,511, Dec. 19, 1996.

[51] Int. Cl.$^6$ ........................................ A61N 1/05
[52] U.S. Cl. ........................................ 607/116; 607/122
[58] Field of Search ........................ 607/115, 116, 607/119, 122, 123

[56] References Cited

U.S. PATENT DOCUMENTS

| | | |
|---|---|---|
| 4,608,986 | 9/1986 | Beranek et al. . |
| 4,677,990 | 7/1987 | Neubauer . |
| 5,246,014 | 9/1993 | Williams et al. . |
| 5,303,704 | 4/1994 | Molacek et al. . |
| 5,584,873 | 12/1996 | Shoberg et al. . |
| 5,676,694 | 10/1997 | Boser et al. . |

FOREIGN PATENT DOCUMENTS

| | | |
|---|---|---|
| 0329112 | 11/1989 | European Pat. Off. . |
| 0622089 | 8/1994 | European Pat. Off. . |
| 9635475 | 11/1996 | WIPO . |

*Primary Examiner*—Scott M. Getzow
*Attorney, Agent, or Firm*—Reed A. Duthler; Harold R. Patton

[57] ABSTRACT

An improved lead body for implantable leads comprising a longitudinally extending core section provided with longitudinally extending grooves in which conductors are located and an outer tubular member, encasing the core and conductors.

20 Claims, 6 Drawing Sheets

MEDICAL ELECTRICAL LEAD

This application claims the benefit of U.S. Provisional Application Ser. No. 60/033,511, filed Dec. 19, 1996.

BACKGROUND OF THE INVENTION

The present invention relates to medical electrical leads, generally, and more particularly to implantable medical leads employing multiple conductors.

Typically, implantable medical leads carrying multiple conductors have either employed lead bodies formed of extruded, multiple lumen tubing or have employed a coaxial structure, in which single lumen tubes are mounted coaxially around one another to define multiple lumens in which conductors may be located.

SUMMARY OF THE INVENTION

The present invention is directed toward an improved lead body construction for use in conjunction with implantable medical leads. The lead body is formed of separate parts including an extruded core or strut member which is provided with longitudinally extending grooves in which conductors may be located and an outer tubing member, surrounding the core. The outer tubing and the core together define multiple lumens in which conductors may be located. This construction simplifies the manufacture of the leads, as it allows the conductor simply to be laid in the elongated grooves of the core, rather than requiring that they be pushed or pulled along the lengths of preformed lumens. In some embodiments of the invention, the core is provided with a central, reinforcing strand, extending along the length of the lead, providing for structural integrity and high tensile strength. The core may be manufactured as a single extrusion, extending the entire length of the lead, or may take the form of sequentially aligned multiple extrusions of differing materials to provide for differential flexibility along the length of the lead.

DETAILED DESCRIPTION OF THE PREFERRED EMBODIMENTS

Figure 1:
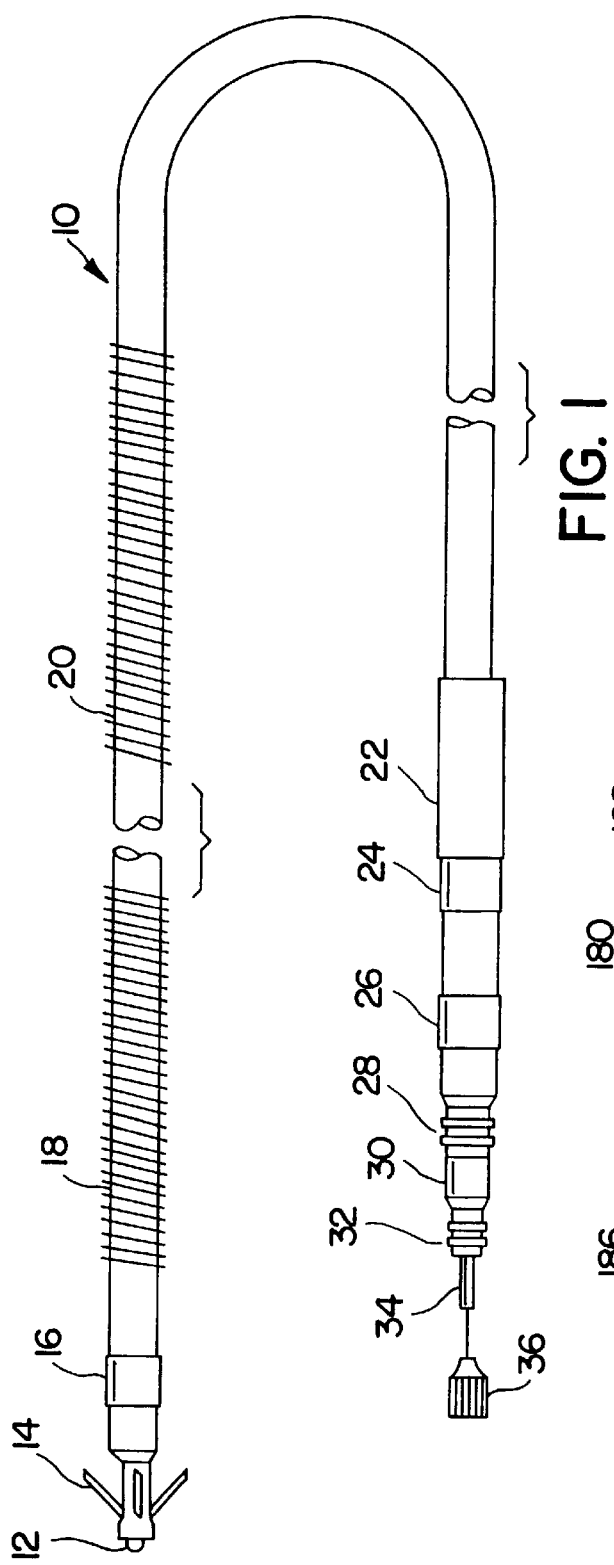
FIG. 1 is a plan view of an implantable lead of the type in which the invention may be practiced.

FIG. 1 is a plan view of an implantable defibrillation lead, employing the present invention. The lead is provided with an elongated insulative lead body 10, which is fabricated according to the present invention, and described in more detail below. At the distal end of the lead is a pacing electrode 12, extending from an insulative tine sheath 14. Proximal to tine sheath 14 are a ring electrode 16 and two elongated coil defibrillation electrodes 18 and 20. Each of the electrodes is coupled to an elongated conductor located within lead body 10 and extending to connector assembly 22. Connector assembly 22 carries three connector rings 24, 26 and 30, and a proximal connector pin 34. Connector rings 24 and 26 are coupled to the conductors which are coupled to defibrillation coil electrodes 18 and 20. Connector ring 30 is coupled to ring electrode 16 and connector pin 34 is coupled to pacing electrode 12. Sealing rings 32 and 28 provide for fluid seals, within the connector block of an implanted pacemaker/cardioverter/defibrillator. A stylet 36 is shown extending from connector pin 36. Manufacture of the electrodes 12, 16, 18 and 20 and connector assembly 22 may be accomplished using any of the conventional methods presently employed to produce implantable pacing and defibrillation leads. In conjunction with embodiments of the present invention which employ bundled, stranded conductors, interconnection of the conductors to the electrodes and connector rings may be accomplished by crimping, swaging and/or welding, as known to the art. In particular, interconnection of bundled, stranded conductors to connectors and electrodes may be accomplished according to U.S. patent application Ser. No. 08/439,332, filed May 11, 1995 by Swoyer et al., U.S. Pat. No. 5,676,694 to Boser et al, issued Oct. 14, 1997, or issued U.S. Pat. No. 5,246,014 issued to Williams et al, all incorporated herein by reference in their entireties.

Figure 2:
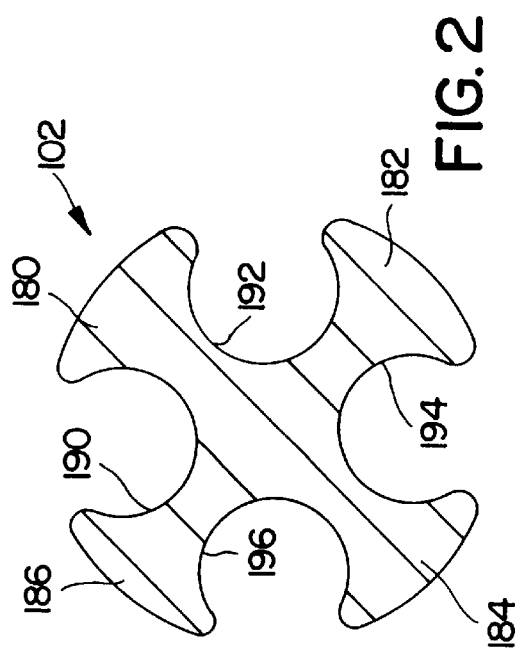
FIG. 2 is a cross-section of one embodiment of an extruded core for use in practicing the invention.

FIG. 2 is a cross-section of a preferred embodiment of the strut or core member portion of the lead body illustrated in FIG. 1. Core 102 is provided with four radially extending portions 180, 182, 184 and 186 which extend longitudinally along the length of the core, and which in turn define four longitudinally extending grooves, 190, 192, 194 and 196. As visible in FIG. 2, it can be seen that the grooves, 190, 192, 194 and 196 are generally circular in cross-section, and that their width at the outer periphery of core 102 is less than their maximum width internal to core 102. This construction allows for insulated conductors which have an outer diameter corresponding to the maximum width of the grooves to be snapped into the groove, as part of the construction process. This mechanism greatly simplifies construction, as the insulated conductors, once snapped into the grooves, will remain there without additional measures during the remainder of the assembly process, during which the assembled core and conductors are slid into the outer tubular portion of the lead body.

Figure 3:
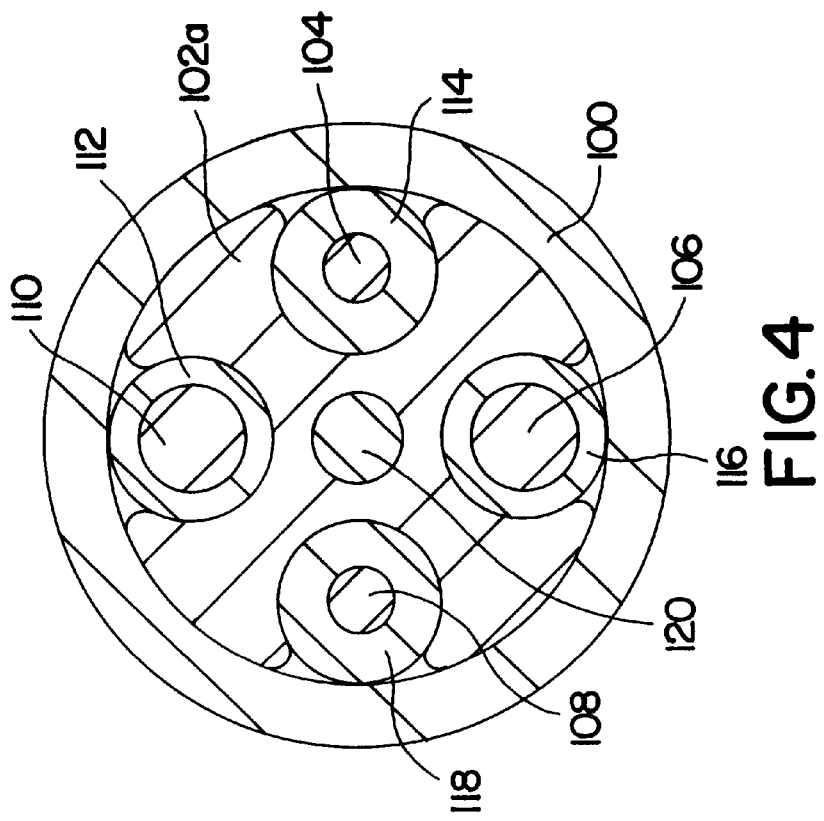
FIGS. 3–6 are cross-sections of leads practicing the invention, employing a core generally as illustrated in FIG. 2.

FIG. 3 shows a cross-section through a lead body employing the core 102 illustrated in FIG. 2. An outer, insulative tube 100 is shown surrounding core 102, defining four lumens in which four insulated conductors 104, 106, 108 and 110 are located. Each of these conductors may take the form of a bundled, stranded conductor as described in the above cited patents and applications or in pending U.S. Pat. No. 5,584,873 to Shoberg et al or U.S. patent application Ser. No. 08711,829 filed Sept. 10, 1996 by Laske et al, both of which are incorporated herein by reference in their entireties. The invention may also be practiced using any of the numerous other stranded conductors known to the art and may also be usefully practiced using coiled conductors, which similarly could be snapped into the grooves in core 102. As illustrated, although the conductors have varying diameters in accordance with the amount of current they are intended to carry, each is provided with an outer insulative sheath, 112, 114, 116 and 118, which provides an overall diameter for the insulated conductors which is equal in each case, and corresponds to the maximum widths of the grooves in which the conductors are located. By this mechanism, a single core member may accommodate a wide variety of conductor types and sizes, allowing for the production of a variety of lead bodies all employing the same core and outer tube.

In the lead illustrated in FIG. 3, the core may be extruded from a different plastic than the outer tube 100. For example, in the context of implantable pacing and defibrillation leads, an inner core 102 fabricated of a polyurethane and outer tube of silicone rubber, is to be particularly desirable. The core and tube may also be fabricated of the same material. The particular durometers of the various plastics chosen may be varied in order to provide desired mechanical characteristics. In the context of implantable pacing and defibrillation leads, the use of silicone rubber insulation on the insulated conductors is believed particularly desirable, in that it does not exhibit cold flow or creep, and thus will not allow for migration of the conductors through the insulation due to repeated flexing of the lead body. In the context of a lead not intended for use under conditions in which repeated flexing occurs, other insulator materials such as polyurethane, polytetraflouroethylene, and so forth, may also be employed.

Tube 100 has an inner diameter approximately equal to the outer diameter of core 102. Tube 100 may be expanded by a suitable chloroflourocarbon or hydrocarbon swelling agent prior to inserting core 102 therein. Alternatively, tube 102 may be expanded by means of air pressure applied at one end while the other end is sealed. If the frictional interference between tube 100 and core 102 permits, use of a lubricant such as alcohol may be sufficient to facilitate insertion of the core. In most embodiments of the invention, use of adhesive to bond the core to the tube will be unnecessary.

Figure 4:
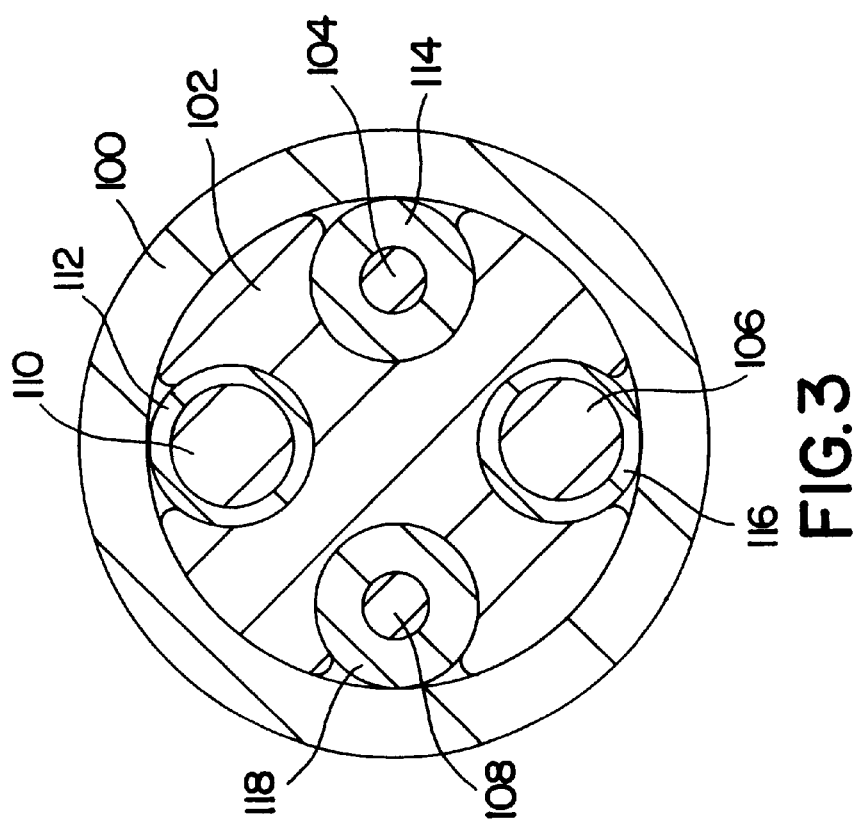

FIG. 4 is a cross-section through an alternative embodiment of a lead employing the present invention. All elements of the lead illustrated in FIG. 4 correspond to the identically numbered elements of the lead illustrated in FIG. 3 with the exception that a modified central core 102a is provided, which has located therein a reinforcing cord 120, which extends the length of the lead, which may be fabricated, for example, of polyethylene terepthalate, polyester or other high tensile strength fiber. In embodiments in which the lead body is manufactured of relatively soft plastics of low tensile strength, reinforcement 120 is particularly desirable. Reinforcement 120 is also valuable in conjunction with embodiments of the lead which employ a core manufactured of discrete segments of differing plastics, to provide for flexibility transitions along the length of the lead, as noted above.

Figure 5:
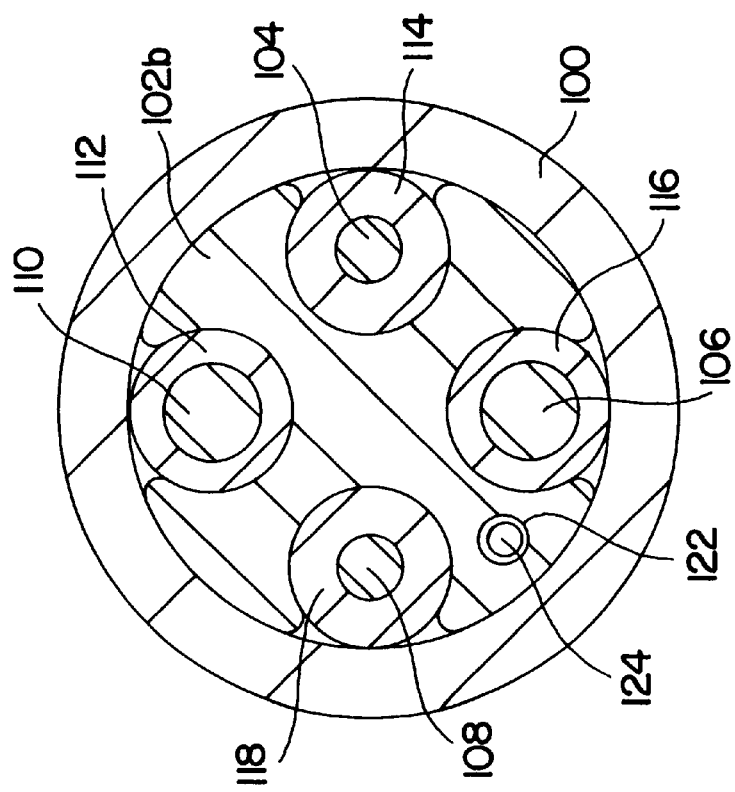

FIG. 5 is a cross-section through an additional alternative embodiment of a lead employing the present invention. All labeled elements of FIG. 5 correspond to identically numbered elements in FIG. 3 with the exception that a modified core 102b is provided which contains an off-center lumen 122 in which a tensile member 124 is located. Tensile member 124 may be, for example, a pull wire coupled to the tip of the lead, such that traction on the pull wire causes deflection of the tip of the lead in the manner described in U.S. Pat. No. 4,677,990, issued to Neubauer, also incorporated herein by reference in its entirety. In conjunction with this type of embodiment, it may also be desirable to employ a flexibility transition as discussed above in conjunction with FIG. 4, providing a more flexible distal tip and thereby confining the location of the deflection to the more flexible portion of the lead. As noted above, in embodiments including multiple part cores, the inclusion of a reinforcement strand may also be desirable.

Figure 6:
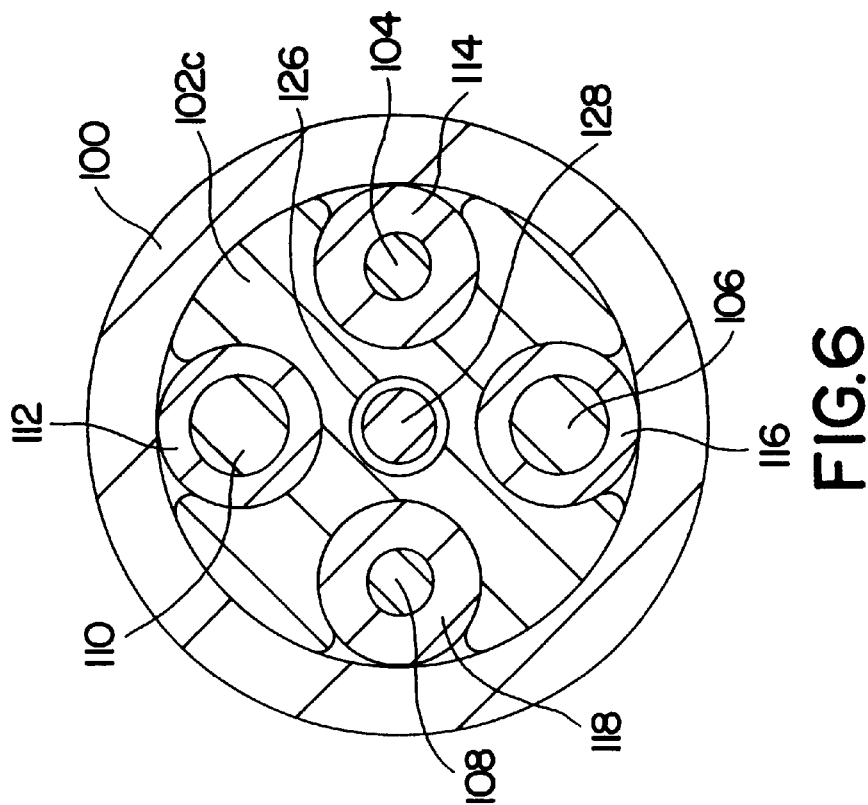

FIG. 6 illustrates yet another embodiment of a lead employing the present invention. All elements of FIG. 6 correspond to identically numbered elements illustrated in FIG. 3, with the exception that modified core element 102c is provided which is provided with a central lumen 126 in which a stylet 128 is located. Stylet 128 may be employed to advance the lead through the vascular system, or in the context of a neurological lead, to advance the lead within the spinal column, it is preferably coated with polytetraflouroethylene or parylene in order to decrease the friction associated with its passage through lumen 126 and reduce the likelihood of puncturing core 102c.

Figure 7:
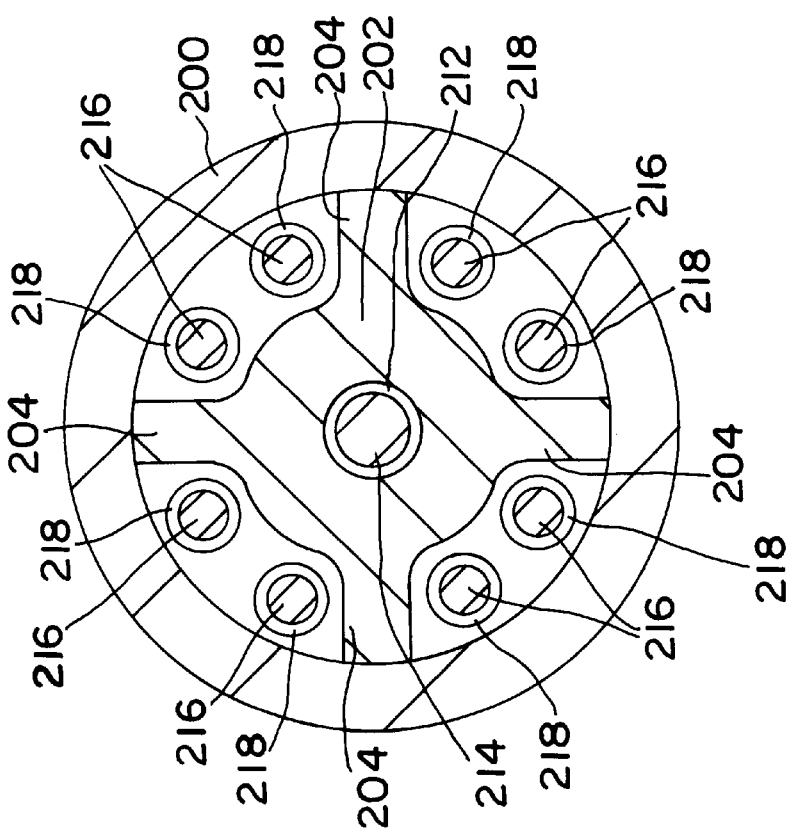

FIG. 7 is a cross-section through an alternative embodiment of a lead employing the present invention. The construction of the lead of FIG. 7 is believed particularly adaptable, for example, to an implantable neurological lead of the type that might be inserted into the spinal column for pain relief. Similar to the embodiments described above, the lead body comprises an outer insulative tube 200 and an inner core 202, which is provided with four radially extending portions 204 which in turn define four longitudinally extending grooves, in which insulated conductors 216 are located. In this embodiment, however, the grooves defined are substantially larger than the insulative conductors, and in fact, are large enough to accommodate multiple conductors. In this embodiment, the conductors may similarly be formed of bundled or stranded wires, provided with an outer insulative coating to 18. The outer insulative coating to 18 may be polytetraflouroethylene, polyurethane, silicone rubber or other biocompatible plastic. A central lumen 212 is provided for passage of a polytetraflouroethylene coated stylet 214.

Figure 8:
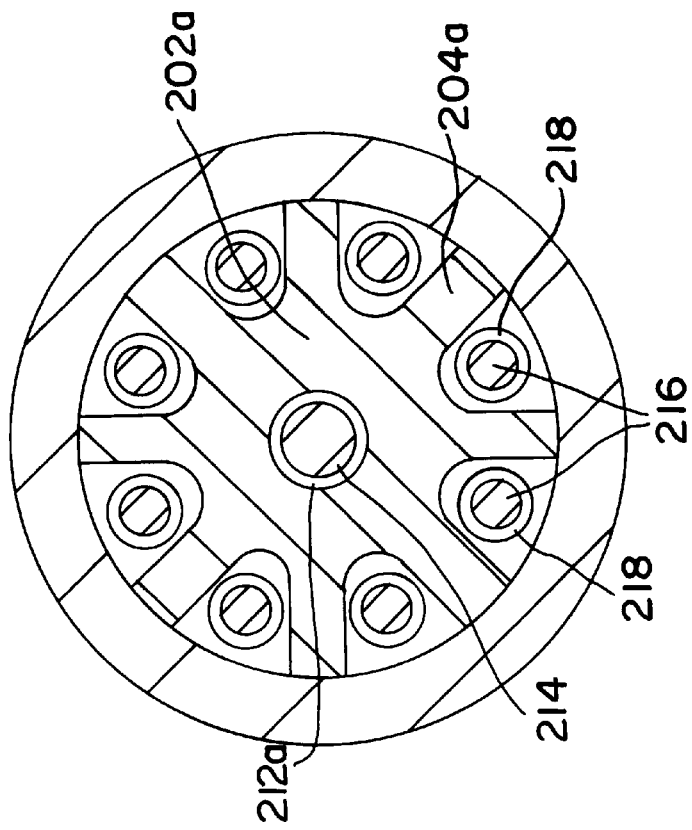
FIGS. 7 and 8 are cross-sections through alternative embodiments of leads according to the present invention.

FIG. 8 shows an alternative embodiment to the lead body construction of FIG. 7. In this view, components correspond to identically numbered components in FIG. 7, with the exception that a modified core 202a is provided, which is provided with eight radially extending portions 204a which in turn define eight longitudinally extending grooves in which individual insulated conductors 216 are located. A central lumen 212a is provided allowing for passage of a polytetraflouroethylene coated stylet 214.

Figure 9:
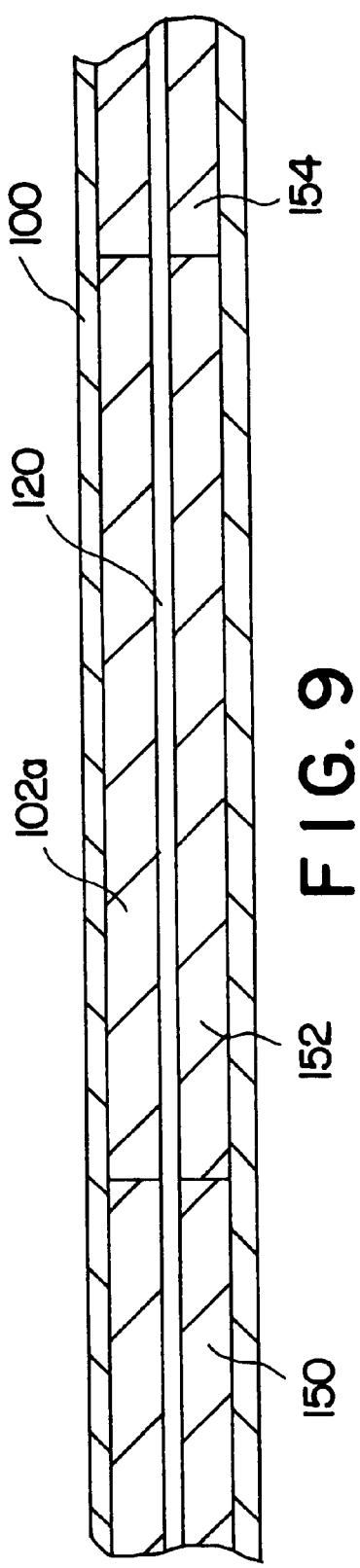
FIG. 9 is a sectional view along the length of a lead corresponding to that illustrated in FIG. 4.

FIG. 9 is a sectional view through a lead as illustrated in FIG. 4, employing a central reinforcing strand 120. In this embodiment, the core 102a takes the form of multiple sections 150, 152 and 154 which are structurally identical to one another, but are extruded of differing materials. For example, if a change in flexibility is desired along the length of the lead, core members fabricated of polyurethanes of differing hardness may be employed. For example, available polyurethanes for implantable leads include polyurethanes having durometers ranging from 55D through 90A. As noted above, this flexibility transition may particularly desirable in the context of the device employing a pull wire, to provide a more flexible distal portion which in turn limits the deflection caused by the pull wire to the distal portion of the lead.

Figure 10:
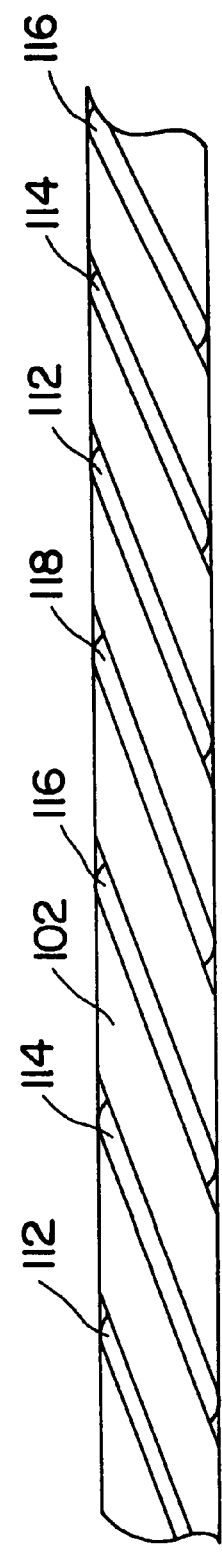
FIG. 10 is a view of a core as illustrated in FIG. 2 with conductors mounted, which has been twisted, prior to application of the outer tube portion of the lead body.

FIG. 10 illustrates an alternative method of production of a lead according to the present invention. The core 102 corresponds to that illustrated in FIG. 3, and the outer insulation 112, 114, 116 and 118 of the conductors illustrated in FIG. 3 can be seen located within the grooves of core 102. However, this view illustrates that the core 102 may be twisted prior to its insertion into outer tubular member 100, so that the assembled body will define longitudinally extending helical lumens, increasing the resistance of the lead body to fracture of the conductors due to repeated flexing. The twisted core 102, if fabricated of polyurethane, may be heated to cause the twisted configuration to become set, prior to assembly. Alternatively, the twisted configuration may be maintained by means of adhesives, coupling the core 102 to the outer tubing 100, so that the outer tubing maintains the core in its twisted configuration.

Figure 11:
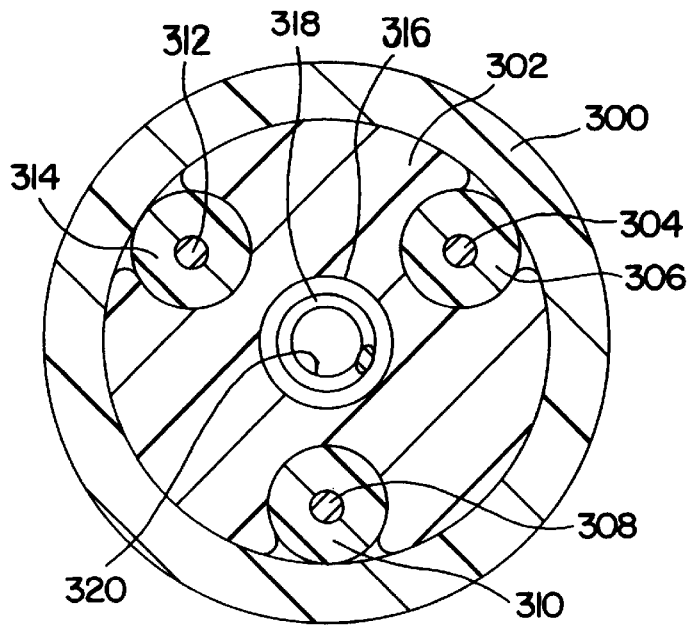
FIG. 11 is a cross-section through an additional alternative embodiment of a leads according to the present invention.

FIG. 11 illustrates a cross-section through an additional alternative embodiment of the lead according to the present invention. In this embodiment, the core 302 is provided with three longitudinally extending grooves carrying conductors 304, 308 and 312. Conductors 304, 308 and 312 are provided with insulative sheaths 306, 310 and 314. In this embodiment, the fourth conductor takes the form of a conventional coiled conductor 318 located in a central lumen 316 within core 302. This embodiment is particularly desirable for use in conjunction with embodiments which might employ an advanceable fixation helix rotated by means of conductor 316, as disclosed in U.S. Pat. No. 4,106,512 issued to Bisping and incorporated herein by reference in its entirety. The interior lumen 320 of coiled conductor 318 may serve as a passage for insertion of a stylet used to position the lead.

Figure 12:
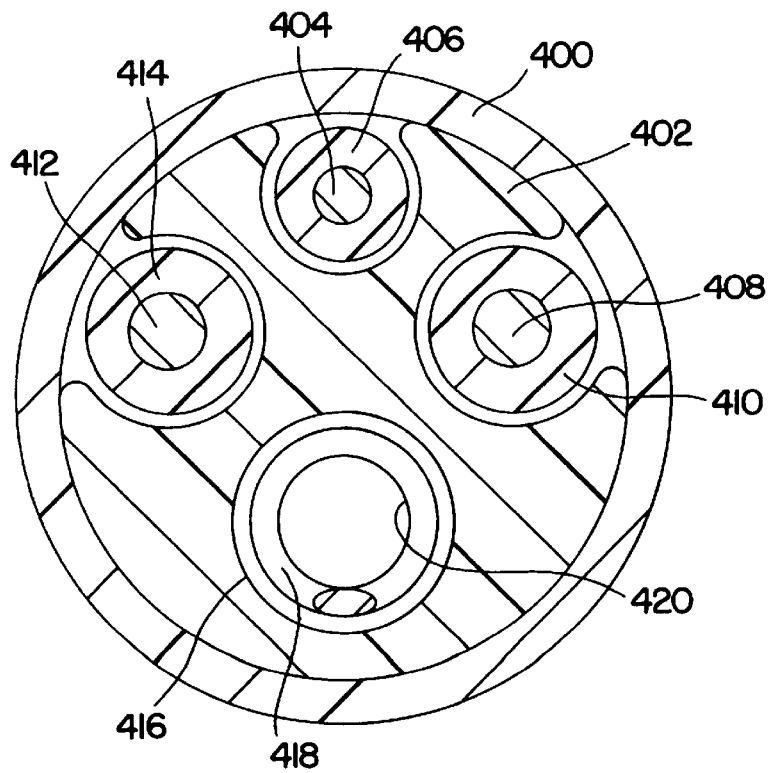
FIG. 12 is a cross-section through an additional alternative embodiment of a leads according to the present invention.

FIG. 12. is a cross-sectional view through an additional alternative embodiment of the lead according to the present invention. In this embodiment, the core 402 is provided with three longitudinally extending grooves carrying conductors 404, 408 and 412, each of which is provided with an insulative sheath 406, 410 and 414 respectively. Core 402 is also provided with an eccentrically located lumen 416 carrying a coiled conductor 418. Coiled conductor 418 is wound to define an internal lumen 420 which allows for passage of a stylet which may be used to assist in positioning the lead. Coiled conductor 418 may be coupled to a fixed electrode as illustrated in the lead in FIG. 1 or alternatively may be coupled to an advanceable helical electrode as disclosed in the above cited Bisping patent.

Although the illustrative embodiment of FIG. 1 is a lead in which all conductors are coupled to electrodes, it should be understood that the lead body construction of the present invention is equally applicable to leads carrying other types of sensors, such as pressure sensors, temperature sensors and the like, as well as being applicable to leads which carry other types of electrically powered devices.

In conjunction with the above disclosure, we claim:

1. A medical electrical lead, comprising an elongated lead body carrying multiple conductors, wherein the lead body comprises:
    an inner, core having radially extending portions extending to an outer periphery of the core and defining one or more longitudinally extending grooves therebetween along the length of the core, the grooves having a width at the outer periphery and a width inward from the outer periphery;
    an outer tubular member surrounding the core; and
    conductors located in one or more of the longitudinally extending grooves of the core.

2. A lead according to claim 1 wherein the width of the longitudinally extending grooves at the outer periphery of the core is less than the width of the grooves inward from the outer periphery of the core.

3. A lead according to claim 2 wherein the conductors have diameters which are greater than the widths of the grooves at the outer periphery of the core, whereby the conductors may be snapped into the grooves.

4. A lead according to claim 3 wherein the conductors comprise at least two insulated conductors each comprising a layer of insulation surrounding an internal conductive member having a diameter, wherein the diameters of the insulated conductors are the same while the diameters of the conductive members differ.

5. A lead according to claim 1 wherein the core comprises two or more core portions fabricated of materials having different mechanical properties, joined end to end.

6. A lead according to claim 1 or claim 5, further comprising a reinforcement extending longitudinally through the core.

7. A lead according to claim 1 wherein the core and the outer tubular member are fabricated of different materials.

8. A lead according to claim 1 wherein the core further comprises a longitudinal conductor lumen and wherein the lead further comprises an additional conductor located in the longitudinal conductor lumen.

9. A lead according to claim 1 wherein the radially extending portions define one or more longitudinally extending grooves therebetween which spiral around the outer periphery of the core.

10. A lead according to claim 9 wherein the core is a plastic member having generally linear longitudinally extending grooves, twisted to cause the grooves to spiral around the outer periphery of the core.

11. A method of making a medical electrical lead, comprising:
    obtaining an inner core having radially extending portions extending to an outer periphery of the core and defining one or more longitudinally extending grooves therebetween along the length of the core, the grooves having a width at the outer periphery and a width inward from the outer periphery;
    locating conductors in one or more of the longitudinally extending grooves of the core; and
    thereafter surrounding the core and conductors with an outer tubular member.

12. A method according to claim 11 wherein the step of obtaining the core comprises obtaining a core having longitudinally extending grooves with widths grooves at the outer periphery of the core less than the widths of the grooves inward from the outer periphery of the core.

13. A method according to claim 12 wherein step of locating conductors in one or more of the longitudinally extending grooves of the core comprises locating conductors which have diameters which are greater than the widths of the grooves at the outer periphery of the core, by snapping the conductors into the grooves.

14. A method according to claim 11 wherein step of obtaining a core comprises obtaining a core having two or more core portions fabricated of materials having different mechanical properties, joined end to end.

15. A method according to claim 11 or claim 14, further comprising the step of providing a reinforcement extending longitudinally through the core.

16. A method according to claim 11 wherein the step of surrounding the core comprises surrounding the core with a tubular member are fabricated of a material different from that of the core.

17. A method according to claim 11 wherein the step of obtaining a core comprises obtaining a core having a longitudinal lumen, further comprising the step of locating an additional conductor in the longitudinal lumen.

18. A method according to claim 11 wherein the step of obtaining a core comprises obtaining a core having radially extending portions which define one or more grooves which spiral around the outer periphery of the core.

19. A method according to claim 11 further comprising the step of twisting the core to cause the grooves to spiral around the outer periphery of the core.

20. A method according to claim 11 wherein locating step comprises locating at least two insulated conductors each comprising a layer of insulation surrounding an internal conductive member having a diameter, wherein the diameters of the insulated conductors are the same while the diameters of the conductive members differ.

* * * * *